US012228501B2

(12) United States Patent
Frish et al.

(10) Patent No.: US 12,228,501 B2
(45) Date of Patent: Feb. 18, 2025

(54) SYSTEM AND METHOD FOR SIMULTANEOUS HIGH-SENSITIVITY MEASUREMENT OF METHANE AND ETHANE VIA LASER ABSORPTION SPECTROSCOPY IN AN OPEN-AIR CONFIGURATION

(71) Applicant: HEATH CONSULTANTS INCORPORATED, Houston, TX (US)

(72) Inventors: Michael B. Frish, Medford, MA (US); Shin-Juh Chen, Arlington, MA (US); Nicholas F. Aubut, Raymond, NH (US); Richard T. Wainner, Somerville, MA (US)

(73) Assignee: Heath Consultants Incorporated, Houston, TX (US)

( * ) Notice: Subject to any disclaimer, the term of this patent is extended or adjusted under 35 U.S.C. 154(b) by 217 days.

(21) Appl. No.: 17/959,798

(22) Filed: Oct. 4, 2022

(65) Prior Publication Data

US 2023/0107797 A1    Apr. 6, 2023

Related U.S. Application Data

(60) Provisional application No. 63/251,949, filed on Oct. 4, 2021.

(51) Int. Cl.
*G01N 21/3504* (2014.01)
*G01N 21/31* (2006.01)
(Continued)

(52) U.S. Cl.
CPC ......... *G01N 21/3504* (2013.01); *G01N 21/39* (2013.01); *G01N 33/0047* (2013.01);
(Continued)

(58) Field of Classification Search
CPC ............... G01N 21/3504; G01N 21/30; G01N 33/0047; G01N 2021/3125;
(Continued)

(56) References Cited

U.S. PATENT DOCUMENTS 4,489,239 A    12/1984    Grant et al.
6,822,236 B1    11/2004    Nelson et al.
(Continued)

FOREIGN PATENT DOCUMENTS

KR    20160085548 A    7/2016

OTHER PUBLICATIONS

Ye et al., "Mid-infrared dual-gas sensor for simultaneous detection of methane and ethane using a single continuous-wave interband cascade laser", Jul. 25, 2016, Optics Express, vol. 24, No. 15 (Year: 2016).*

(Continued)

*Primary Examiner* — Peter J Macchiarolo
*Assistant Examiner* — John M Royston
(74) *Attorney, Agent, or Firm* — Bracewell LLP; Douglas W. Rommelmann

(57) ABSTRACT

A system for measuring a target gas via laser absorption spectroscopy in an open-air configuration, comprising a mid-infrared distributed feedback interband cascade laser (mid-IR DFB-ICL) having a wavelength selected to correspond with a spectral absorption line of the target gas and first electronic circuitry to control the laser temperature, current and modulation frequency. The mid-IR DFB-ICL is mounted to a heat sink. The system includes an optical component that projects a beam of the mid-IR DFB-ICL onto a distal backscattering directionally-reflective target and an optical receiver assembly that receives a fraction of the laser light that is backscattered from the directionally-reflective target and focuses the collected light onto an (Continued)

uncooled photodetector having a spectral bandwidth and optical configuration selected to optimize signal-to-noise response to received laser light. The optical receiver assembly comprises a primary mirror for receiving laser light backscattered from the directionally-reflective target and focusing the collected light onto the uncooled photodetector.

21 Claims, 12 Drawing Sheets

(51) Int. Cl.
*G01N 21/39* (2006.01)
*G01N 33/00* (2006.01)

(52) U.S. Cl.
CPC ............. *G01N 2021/3125* (2013.01); *G01N 2021/392* (2013.01); *G01N 2021/399* (2013.01)

(58) Field of Classification Search
CPC ....... G01N 2021/392; G01N 2021/399; G01N 2201/0216; G01M 3/38
See application file for complete search history.

(56) References Cited

U.S. PATENT DOCUMENTS

| | | |
|---|---|---|
| 7,075,653 B1 | 7/2006 | Rutherford |
| 8,502,152 B1 * | 8/2013 | Hashmonay ....... G01N 21/3504 250/339.12 |
| 9,797,798 B2 | 10/2017 | Frish |
| 2005/0134859 A1 | 6/2005 | Kalayeh et al. |
| 2006/0044562 A1 | 3/2006 | Hagene et al. |
| 2014/0204382 A1 * | 7/2014 | Christensen ....... G01N 21/3504 356/402 |

OTHER PUBLICATIONS

Nähle et al., "Distributed Feedback Interband Cascade Lasers for Spectroscopy from 3-6 µm", Next-Generation Spectroscopic Technologies VII. vol. 9101. SPIE, 2014. (Year: 2014).*
International Search Report and Written Opinion, Application No. PCT/US2022/045667, dated Jan. 31, 2023.
Aeris Technologies, Inc., "ResponderTM Advanced Mobile LDS", MIRA-Responder-LDS_191208, Dec. 2019, www.aerissensors.com.
ABB Inc., "MobileGuard™ Natural Gas Leak Detection System" brochure, 2020, 8 pages (PB_MobileGuard Brochure-EN_A4.pdf (abb.com)).
Allen et al., "Fuelfinder: Remote Leak Detector for Liquid Hydrocarbons", TR-2996, Physical Sciences Inc., Andover, MA, Jul. 2014.
Chen et al., "Natural Gas Pipeline Leak Rate Measurement System", Final Report, PSI-6663, Aug. 31, 2018, Physical Sciences Inc, pp. 1-4.
Frish et al., "Extended Performance Handheld and Mobile Sensors for Remote Detection of Natural Gas Leaks", Phase II Final Report, PSI-1402/TR-1979, May 2005.
Nanosystems and Technologies GmbH., "DFB Interband Cascade Lasers—(ICL): 2800 nm-4000 nm", nanoplus.com, 2021.
Picarro, Inc., "Picarro Natural Gas Asset Management Solution—Techology Brief", 2019, Picarro.

* cited by examiner

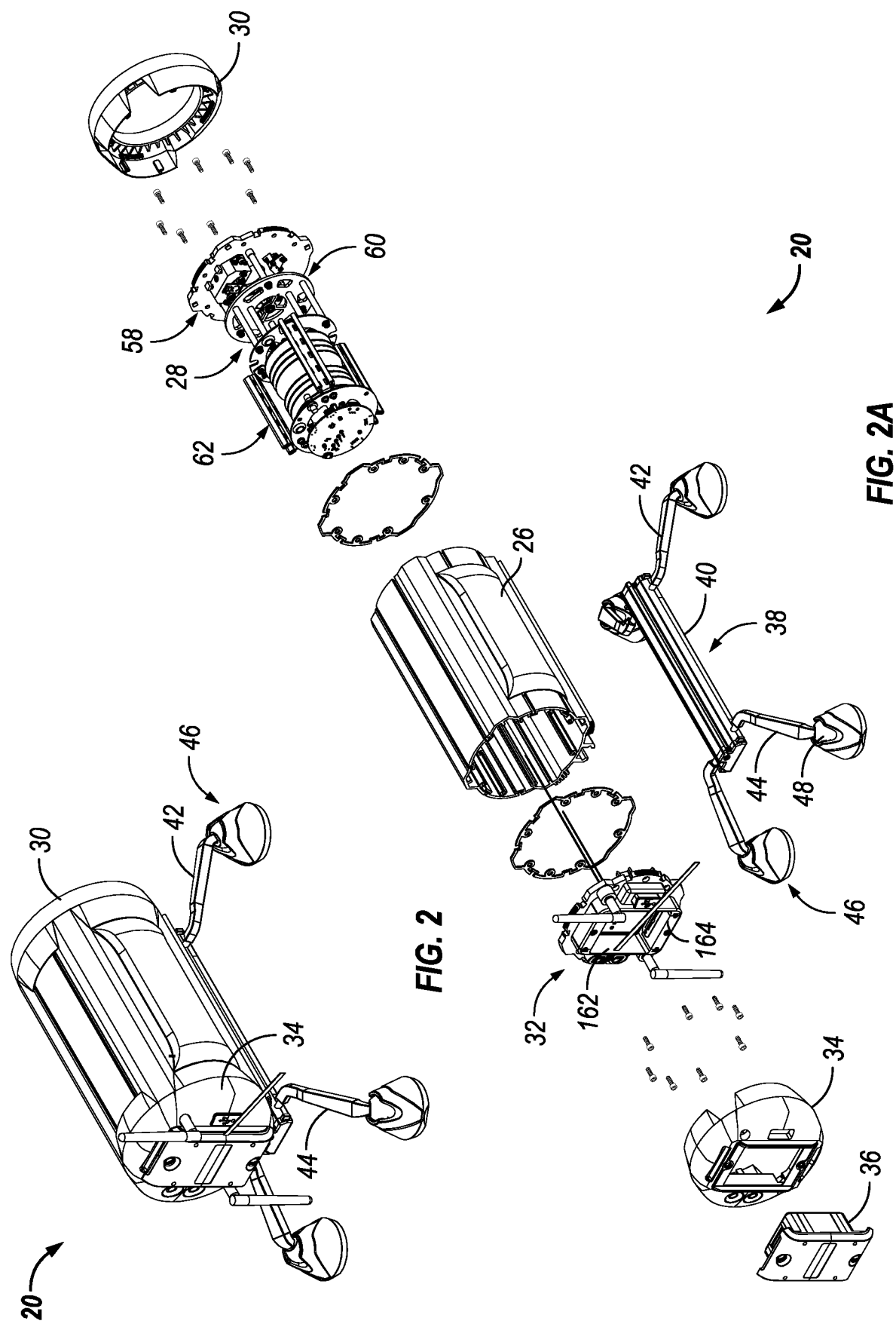

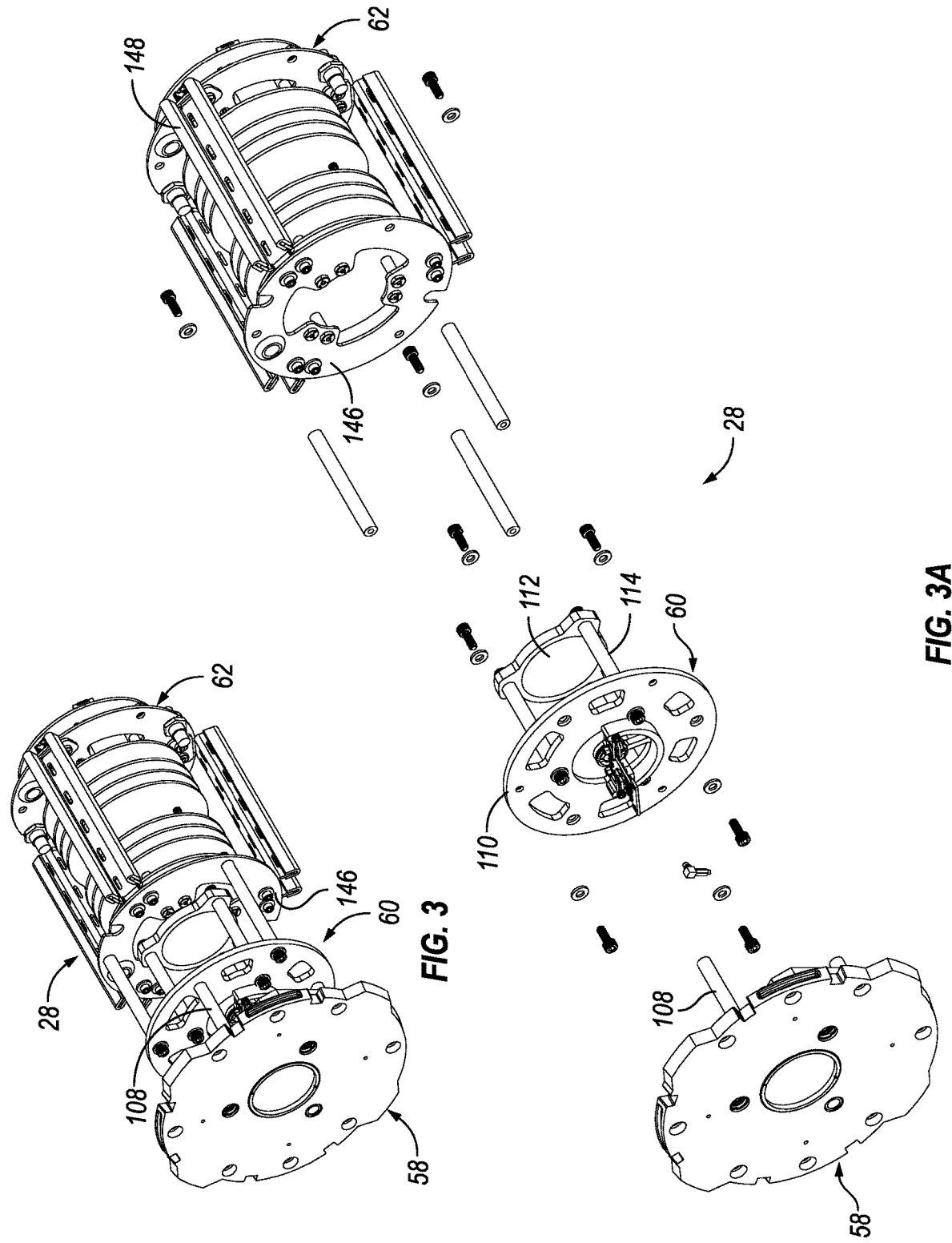

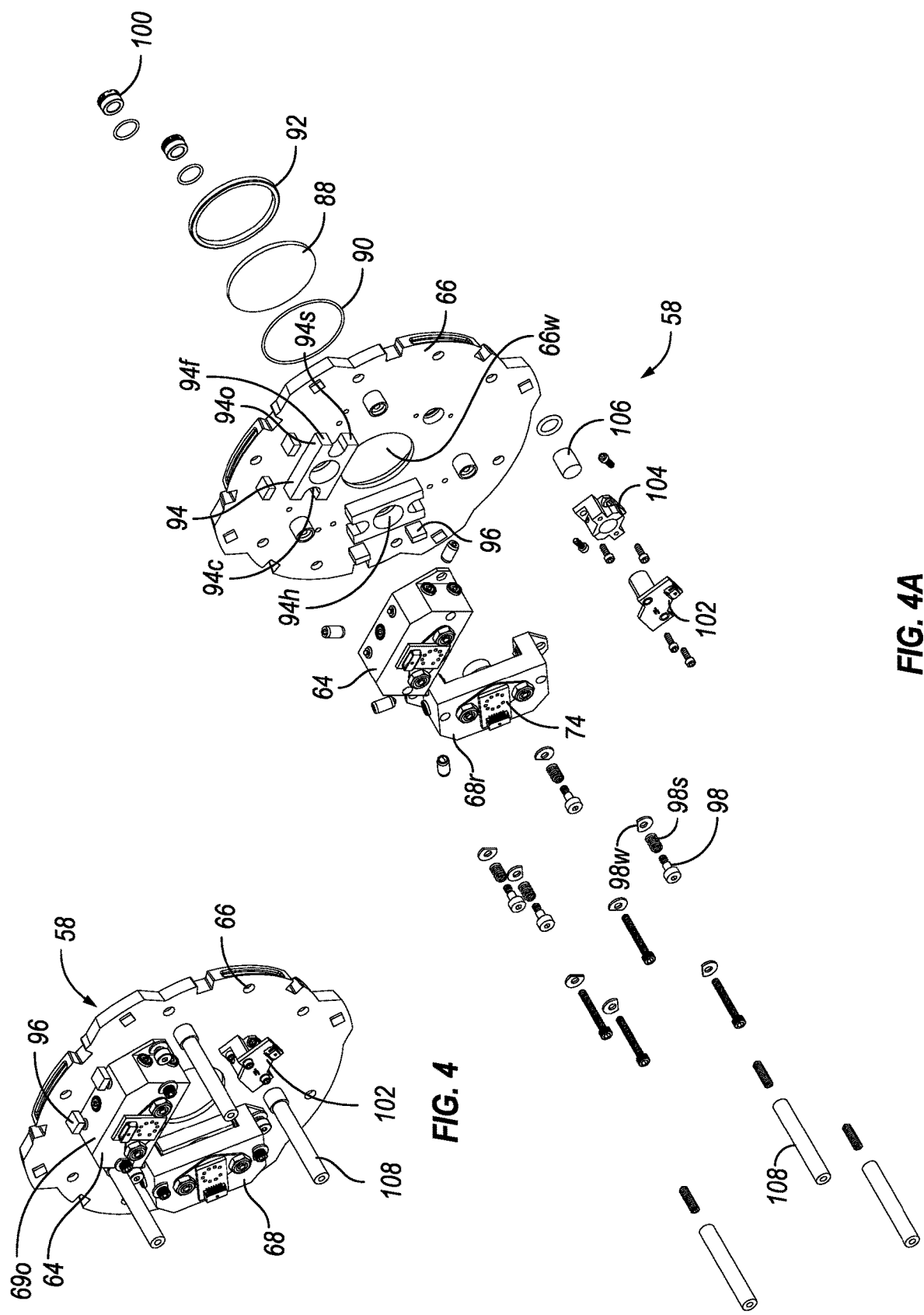

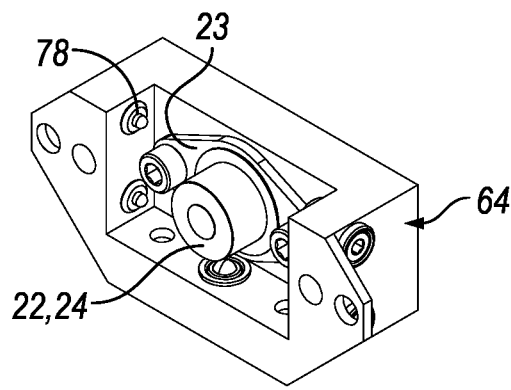
FIG. 5
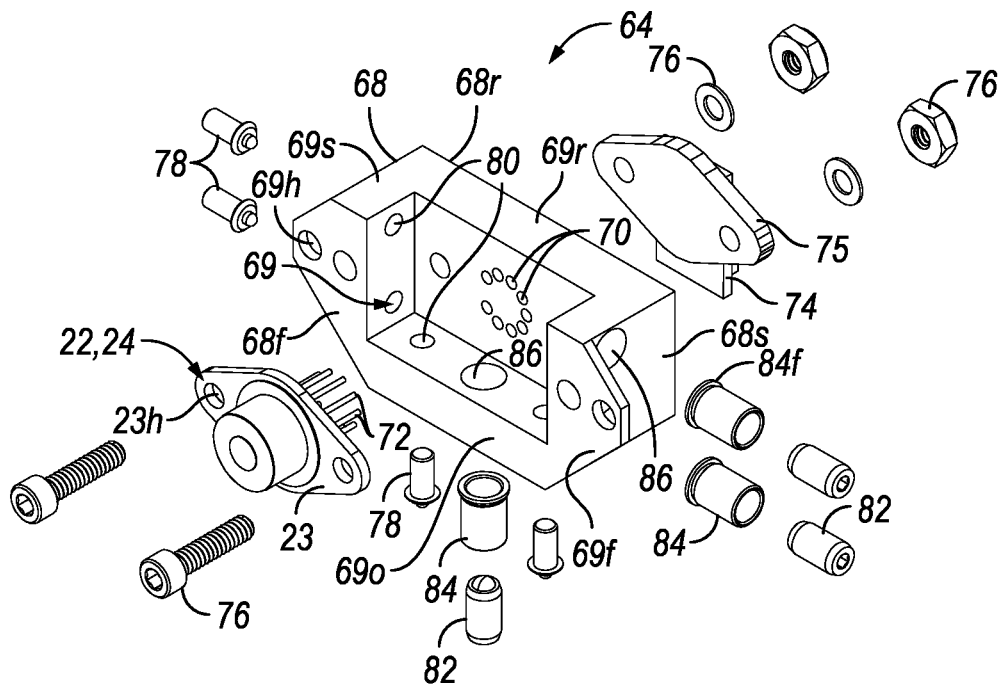
FIG. 5A
FIG. 5B

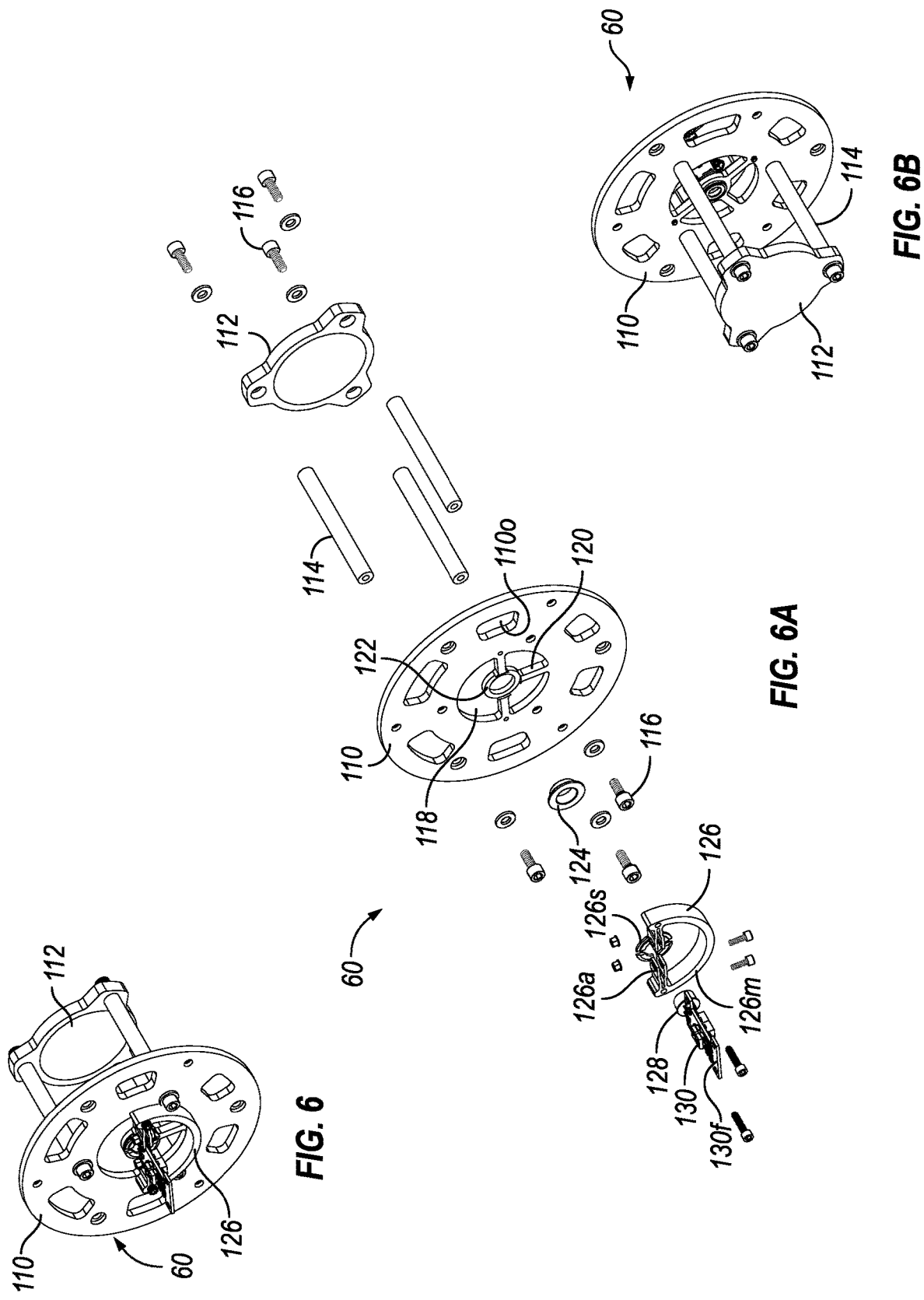

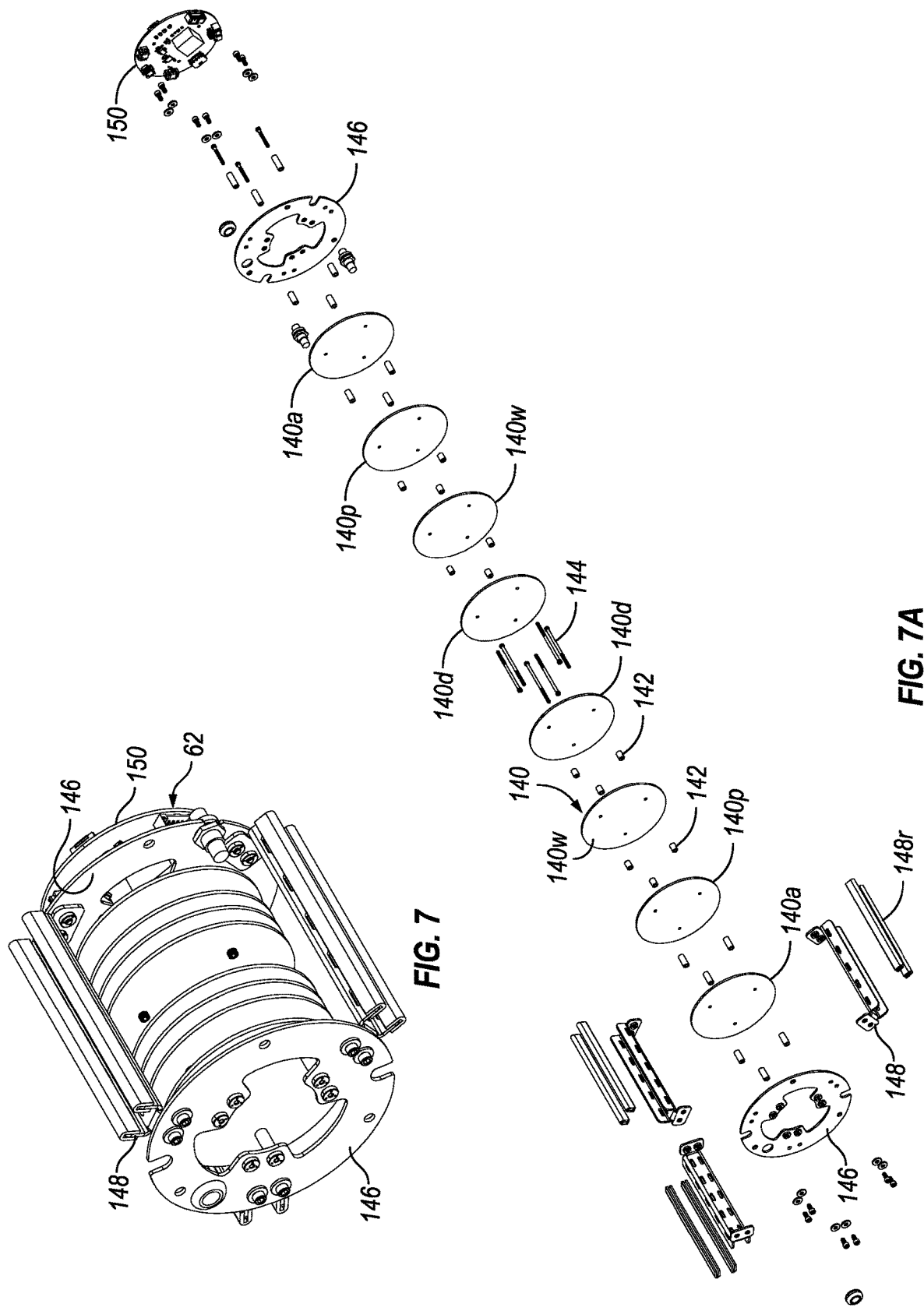

SYSTEM AND METHOD FOR SIMULTANEOUS HIGH-SENSITIVITY MEASUREMENT OF METHANE AND ETHANE VIA LASER ABSORPTION SPECTROSCOPY IN AN OPEN-AIR CONFIGURATION

CROSS-REFERENCE TO RELATED APPLICATIONS

This application claims the benefit of U.S. Provisional Application Ser. No. 63/251,949 filed on Oct. 4, 2021. Applicant incorporates by reference herein Application Ser. No. 63/251,949 in its entirety.

BACKGROUND OF THE INVENTION

1. Field of the Invention

The present invention relates generally to natural gas emission detection and specifically to detections of methane and ethane gas.

2. Description of the Related Art

There exists a problem of deploying cost-effective devices that detect natural gas leaks emanating from pipelines and related gas gathering, transmission, and distribution infrastructure during mobile survey. These devices require high probability of detection and few false detections even when leak sources may be some distance from the mobile survey vehicle route where leaked gas transported by wind into the vehicle's path is of very small concentration. Because natural gas primarily contains methane gas, detecting methane concentrations elevated above the normal ambient level (approximately 2 parts per million) serves as an indicator for detection of natural gas. However, methane may originate from sources other than natural gas (e.g., biogas emitted by swamps, sewers, landfills, etc.). Therefore, technologies that differentiate natural gas from other methane sources are desirable for mobile surveys, particularly for discriminating against false detection of gas leaks. Concurrent measurement of both methane and ethane provides this differentiation, ethane being a component of natural gas but not biogas and not typically present at significant concentration in ambient air.

Natural gas measurement technologies that draw ambient gas (i.e., air) through a measurement cell are current commercial products commonly deployed with leak survey vehicles. Some utilize highly sensitive laser-based sensors combined with the measurement cell. The refresh time of these vehicle-mounted extractive analyzers is typically about 1 second, determined by the flow rate, cell volume, and tubing length. However, the vehicle may pass through a wind-driven emission plume emanating from a local leak source in a small fraction of a second. As a result, the extractive analyzer is unable to resolve the temporal concentration fluctuations inherent to the intermittent "gusts" of wind-driven turbulent plumes. Furthermore, the plume of emitted gas sampled by the extractive analyzer is diluted by ambient air from outside the plume. To avoid missed detections (false negatives), extractive analyzers require exceptionally low Limits of Detection (LoD). Instrumental drift that exceeds the LoD on timescales comparable to the plume detection time may cause false or missed detections.

The assignee, Heath Consultants Inc., has commercialized an open-path optical technique that is used for mobile leak survey. This Optical Methane Detector (OMD) is a sensor that operates by spectral absorption of infrared light by methane in an open air path through which an infrared light beam is transmitted. Many gas molecules absorb energy in narrow bands surrounding specific wavelengths in the electromagnetic spectrum. Methane has strong absorption bands at 1.33 µm, 1.67 µm, 3.3 µm, and 7.6 µm. At wavelengths outside an absorption band, there is essentially no absorption. Thus, the OMD measures the attenuation of an infrared light source passing through a gas sample at the methane-characteristic absorption wavelength to determine the presence of methane gas. The OMD generally uses a short (~1 m) open optical path sample method which eliminates the sampling time delay associated with extractive techniques. In a short open path configuration, the light source is transmitted across a line of sight and is either reflected to an optical detector by a fixed reflector, or the light is received directly by a fixed detector located at the distal end of the open optical path. Using its broadband infrared light source and optical filters to select measurement wavelengths, OMD senses methane concentrations greater than approximately 1 ppm.

Lasers are used as infrared light sources to provide highly sensitive gas detectors sensitive to concentrations as low as ~10 ppb for methane with sub-second response and little cross-sensitivity to gases other than the target gas.

Gas analyzers using Tunable Diode Laser Absorption Spectroscopy (TDLAS) rely on the same well-known spectroscopic principles as OMD and are often coupled with sensitive detection techniques and advanced diode lasers. A TDLAS sensor system incorporates a laser that is continually tuned over time to repetitively scan its wavelength across the bandwidth of a specific target analyte gas absorption line. Upon transmitting the laser beam through a path bearing the target gas, the beam is attenuated according to the Beer-Lambert relation:

$$I(v(t)) = I_t(v(t)) \exp[-S(T)G(v-v_o,T,P)N_g(P_g,P,T)\ell] = I_t(v(t))\exp[-\alpha(v,T,P)] \quad (1)$$

where:
$I_t(v(t))$=laser power transmitted from the source (W)
$I(v(t))$=laser power after propagating through a gas measurement path (W)
t=time (s)
v=laser frequency (reciprocal of wavelength, $cm^{-1}$)
$v_o$=laser frequency at line center ($cm^{-1}$)
$\ell$=length of the measurement path (cm)
$S(T)$=spectral line strength ($cm^{-1}$/molecule-$cm^{-2}$)
T=temperature (K)
$N_g$=number density of target gas molecules (molecules/$cm^3$)
$P_g$=partial pressure of target gas (atm)
P=total pressure of gas sample (atm)
$G(v-v_o,T,P)$=lineshape parameter ($1/cm^{-1}$)

While this wavelength scanning occurs, a photodetector receives the laser power transmitted through the gas. The electrical signal output by the photodetector is proportional to $I(v(t))$.

In Eq. (1), the argument of the exponential function, $\alpha(v,T,P)$, is conventionally known as the absorbance. Its temperature and pressure dependence arises from three sources: 1) the linestrength parameter, $S(T)$, which represents the temperature-dependent Boltzmann population distribution of molecular quantum states; 2) the target gas number density, which is related to target gas partial pressure and temperature by the ideal gas law; and 3) the lineshape parameter, $g(v-v_o,T,P)$, which is a complex function of temperature and pressure resulting from a combination of Doppler and collisional line broadening mechanisms. When the total pressure of the gas sample is sufficiently high, resulting in frequent intermolecular collisions, the lineshape function assumes a Lorentzian form:

$$G(\nu)=[1/\pi g_o P][1/(\{\nu-\nu_o\}/g_o P\}^2+1)] \quad (2)$$

where $g_o$=broadening coefficient ($cm^{-1}$/atm). Eq. (2) shows that the linewidth, $g_o P$, (i.e., the range of wavenumbers spanned between the half-maxima of the lineshape) is proportional to the total pressure of the gas sample. Though not explicit in Eq. (2), $g_o$ is inversely proportional to the square root of temperature, representing the decreasing rate of molecular collisions with increasing temperature at constant pressure.

The assignee, Heath Consultants Inc., has commercialized a laser methane detector under the trademark RMLD®, described in assignee's U.S. Pat. No. 7,075,653, using backscatter TDLAS and wavelength-modulation spectroscopy (WMS). Applicant incorporates by reference herein U.S. Pat. No. 7,075,653 in its entirety. The laser methane detector includes a tunable diode laser, an optical detector, and associated detection circuitry. In what is referred to as a stand-off measurement path, the tunable diode laser beam is transmitted onto a distant (e.g., up to 100 feet) topographic target. Some of the laser light is reflected or backscattered by the target and returns to the optical detector co-located with the laser in the laser methane detector. The system is designed so that the optical detector provides a measurable electrical signal output in response to the received backscattered laser light. The laser has a specific design wavelength (e.g., 1.65 µm, a wavelength corresponding to an absorption line of methane which is also free of interfering absorption from other molecules) chosen to optimize the sensitivity to methane gas using commercially available near-infrared lasers in packages coupling the lasers to optical fibers. The laser's fast tuning capability is exploited to rapidly and repeatedly scan the wavelength across the gas absorption line. While this scanning occurs, the fraction of emitted laser power that is transmitted through the gas mixture and reflected back to the instrument is received and measured by the optical detector. When the wavelength is tuned outside of the narrow characteristic absorption band ("off-line"), the received light is equal to or greater than when it falls within the narrow absorption band ("on-line"). Measurement of the relative amplitudes of off-line to on-line reception yields a precise and highly sensitive measure of the concentration of the methane gas along the path transited by the laser beam. The collected light is converted to an electrical signal, which is processed so that methane column density (the methane concentration integrated over the beam length) can be reported, usually in parts per million meters (ppm-m). Typically, the laser methane detector rapidly processes discreet measurements at a refresh rate, e.g., of 10 Hz.

The mid-infrared spectral region (wavelengths of 3-5 µm) can provide higher sensitivity than near-infrared for some gas sensor applications. It is known that one gas specie (e.g. methane or ethane) can be measured using a mid-infrared (mid-IR) distributed feedback interband cascade laser (DFB-ICL) in an open-air path. Example embodiments include direct illumination of a detector located at the distal end of the open-air path, and backscatter TDLAS with Wavelength Modulation Spectroscopy (WMS). In the latter, the laser beam has been collimated by an off-axis parabolic mirror and projected onto a distal aluminum scattering target. Backscattered laser power is received by 4" diameter mirror and focused onto a liquid-nitrogen cooled InAs detector. WMS is performed by laboratory benchtop electronic tools.

It is further known that methane and ethane can be measured in an extractive configuration using a single mid-IR DFB-ICL operating near room temperature. Via adjustment of laser temperature and current, the laser wavelength is tuned to interrogate either methane or ethane spectral features. This is "time multiplexing." A DFB-ICL is manufactured to allow tuning over a limited range of wavelengths, thus this technique requires selecting ethane and methane spectral features that can both be accessed within the laser's tuning range.

It is further known that two gases may be measured simultaneously using near-IR DFB lasers, each manufactured with its wavelength selected to enable continuous interrogation of a spectral feature of a target gas. In prior art using near-infrared laser sources coupled to optical fiber transmission cables, the laser outputs are combined by fiber optic couplers. At the fiber termination the combined laser beams are directed to either extractive or open-air optical paths. Returned laser light is focused onto a photodetector. In some implementations, the lasers are time-multiplexed as discussed above. In other implementations, the current supplying each laser, and thus the laser wavelength, is modulated at a fixed frequency. Demodulation of the detector signal measures the power at this frequency and its second harmonic. This is the essence of WMS. The two lasers may be modulated at two different frequencies and separately demodulated at those two frequencies. This is Frequency Modulation; it enables simultaneous measurement of the two gases.

It would be desirable to have a cost-effective, compact device that, during mobile survey, detects with high probability of detection and few false detections, small natural gas emissions that may emanate from a distant source.

SUMMARY OF THE INVENTION

The present invention solves the problem of deploying cost-effective devices that, during mobile survey, detects with high probability of detection and few false detections, small natural gas emissions that may emanate from a distant source. A preferred embodiment of the invention is a compact, highly sensitive, fast response open-air sensor system using the backscatter tunable diode laser absorption spectroscopy (TDLAS) technique. The system of the preferred embodiment measures concurrent methane and ethane concentrations, each with better than 100 ppb LoD at 10 Hz. Preferably, the LoD for ethane is better than 10 ppb. The system includes dual-gas sensing capability.

One aspect of the invention is to measure ppb concentrations of methane and ethane simultaneously at high speed using mid-IR backscatter TDLAS with distributed feedback interband cascade lasers (DFB-ICLs) operating near room temperature.

An aspect of the present invention solves a problem of selecting preferred wavelengths of methane and ethane spectral features that enable measuring the targeted ppb concentrations free of cross-sensitivities to other ambient gases such as water and carbon dioxide.

An aspect of the present invention provides a method that solves the additional problem of tuning the laser or lasers to the selected spectral features.

An aspect of the present invention provides a method that solves the problem of combining the laser beams in an open-air backscatter configuration for frequency multiplexing absent fiber-coupling which is not practical with mid-IR lasers.

An aspect of the present invention solves the problem of achieving the desired measurement performance in a package meeting the mobile leak survey mission requirements.

In a preferred embodiment of the invention, the invention comprises an electro-optic package and a laser backscatter target package separated by approximately one meter. The electro-optic and backscatter target packages are suitable for attachment to a natural gas leak survey vehicle.

In one embodiment, the electro-optic package includes two mid-IR DFB-ICLs, with the first laser selected to have a wavelength corresponding with a specific ethane spectral absorption line and the second laser selected to have a wavelength corresponding with a specific methane spectral absorption line. Preferably, the first and second lasers combined with the system optical design and signal processing method provides desired sensitivity to the target gas and is free from cross-sensitivity to non-target gases. The two lasers are selected to emit approximately the same output power. This allows a single detector to receive the backscattered light from the two lasers.

In one embodiment the electro-optic package is configured for example as a cylinder of nominally less than 6 inches diameter and 12 inches length, that may be mounted along the outside surface of a gas utility leak survey vehicle such as a small truck. In an embodiment, mid-IR laser technology provides the needed sensitivity and speed for detecting and measuring methane and ethane. The system's detection speed is fast compared to its drift, an aspect that reduces false detections.

In one embodiment, the system includes a fast open-air configuration that uses no extractive sampling cell, does not dilute the plume with ambient gas drawn from outside the plume during the sampling period, and temporally resolves the intermittent fluctuations in the plume concentration signature. The preferred embodiment of the invention thus enables statistical processing that enhances probability of detecting small leaks as described in U.S. Pat. No. 9,797,798 to Frish. Applicant incorporates by reference herein U.S. Pat. No. 9,797,798 in its entirety.

In one embodiment, the electro-optic package includes an optical transceiver that supports the two lasers on a heat sink platform enabling wavelength-stabilized operation over ambient temperatures of −30 to 50° C. Additionally, the optical transceiver preferably collimates and projects the two laser beams onto a common location on a distal backscatter target and receives a fraction of the laser light that is backscattered from the distal target and focuses the collected light onto an uncooled mercury-cadmium-telluride photodetector with spectral bandwidth and optical configuration selected to optimize signal-to-noise response to received laser light.

Preferably, the electro-optic package includes electronic circuits to operate each laser. The electronic circuitry controls laser temperature and laser current and provides adjustment for both parameters. The combination of laser temperature and current sets the laser wavelength to the designated methane or ethane spectral absorption feature. The circuitry also provides for a continual sinusoidal modulation of laser current, and thus laser wavelength. Preferably, the modulation is set to repeatedly scan the laser wavelength across the spectral absorption feature, thus enabling the sensitive detection technique known as Wavelength Modulation Spectroscopy (WMS). The methane modulation frequency differs from the ethane modulation frequency. This enables separating the signals received by the photodetector and processing them individually in parallel via the technique known as Frequency Multiplexing. Electronic circuitry processes the signals by demodulating the photodetector signals and producing outputs from which target gas concentrations are deduced.

The laser backscatter target package includes a directionally-reflective disk approximately perpendicular to the laser propagation direction. The disk material provides reflectance at the laser wavelengths sufficient to achieve the desired laser power at the photodetector. The target package may preferably include a target attachment platform and a battery-powered motor. The target disk may be in continuous motion by spinning around its axis to reduce the effects of laser speckle on system accuracy.

In one embodiment the invention is a system for measuring a target gas via laser absorption spectroscopy in an open-air configuration, comprising a mid-IR DFB-ICL having a wavelength selected to correspond with a spectral absorption line of the target gas and first electronic circuitry to control the laser temperature, current and modulation frequency. The mid-IR DFB-ICL is mounted to a heat sink. The system includes an optical component that projects a beam of the mid-IR DFB-ICL onto a distal backscattering directionally-reflective target and an optical receiver assembly that receives a fraction of the laser light that is backscattered from the directionally-reflective target and focuses the collected light onto an uncooled photodetector.

Preferably, the photodetector has a spectral bandwidth and optical configuration selected to optimize signal-to-noise response to received laser light.

Preferably, the optical receiver assembly comprises a primary mirror for receiving laser light backscattered from the directionally-reflective target and focusing the collected light onto the uncooled photodetector.

Preferably, the directionally-reflective target comprises a material that provides reflectance at the laser wavelength sufficient to achieve a desired laser power at the photodetector. Preferably, the target material is RC-301112-0000-NP, a product of Safe Reflections, Inc.

In one embodiment, the system further includes second electronic circuits providing for a continual sinusoidal modulation of laser current and wavelength, the continual sinusoidal modulation set to repeatedly scan the laser wavelength across the spectral absorption feature at a selected modulation frequency to enable wavelength modulation spectroscopy, and third electronic circuits to demodulate the photodetector signal and produce outputs from which target gas concentrations are deduced.

Preferably, the open-air path length of the laser beam is approximately one meter and the laser wavelength is selected to provide a desired sensitivity to the target gas and is substantially free from cross-sensitivity to non-target gases.

Another embodiment of the invention is a system for simultaneously measuring methane and ethane in an open-air configuration comprising a first mid-IR DFB-ICL having a wavelength selected to correspond with a spectral absorption line of ethane and a second mid-IR DFB-ICL having a wavelength selected to correspond with a spectral absorption line of methane. First electronic circuitry controls the first laser temperature, current and modulation frequency and second electronic circuitry controls the second laser temperature, current and modulation frequency. The first and second mid-IR DFB-ICLs are mounted to a heat sink. A first optical component projects a beam of the first mid-IR DFB-ICL onto a distal backscattering directionally-reflective target and a second optical component projects a beam of the second mid-IR DFB-ICL onto the distal backscattering directionally-reflective target. An optical receiver assembly receives a fraction of the laser light that is backscattered from the directionally-reflective target and focuses the collected light onto an uncooled photodetector. Preferably, the modulation frequency of the first mid-IR laser differs from that of the second mid-IR laser.

Preferably, the beam projected from the first mid-IR DFB-ICL and the beam projected from the second mid-IR DFB-ICL substantially overlap each other at the distal backscattering directionally-reflective target.

Preferably, the first and second mid-IR DFB-ICLs, the first and second electronic circuitry, the first and second optical components, the optical receiver assembly and the heat sink are arranged in a compact package adapted for mounting to a natural gas utility leak survey vehicle.

BRIEF DESCRIPTION OF THE SEVERAL VIEWS OF THE DRAWINGS

The invention is better understood by reading the detailed description of embodiments which follows and by examining the accompanying drawings, in which:

FIG. 2 is a perspective view of an electro-optic package according to an embodiment of the invention;

FIG. 2A is an exploded view of the electro-optic package of FIG. 2;

FIG. 3 is a perspective view of an electro-optic internal assembly shown in FIG. 2A;

FIG. 3A is an exploded view of the electro-optic internal assembly shown in FIG. 3;

FIG. 4 is a perspective view of a transmitter plate assembly shown in FIG. 3;

FIG. 4A is an exploded view of the transmitter plate assembly shown in FIG. 4;

FIG. 5 is a perspective view of a laser mount subassembly shown in FIG. 4;

FIG. 5A is an exploded view of the laser mount subassembly shown in FIG. 5;

FIG. 5B is a second perspective view of the laser mount subassembly;

FIG. 6 is a perspective view of an optical receiver assembly shown in FIG. 3A;

FIG. 6A is an exploded view of the optical receiver assembly shown in FIG. 6;

FIG. 6B is a second perspective view of the optical receiver assembly;

FIG. 7 is a perspective view of a printed circuit board stack subassembly shown in FIG. 3;

FIG. 7A is an exploded view of the printed circuit board stack subassembly shown in FIG. 7;

DESCRIPTION OF THE PREFERRED EMBODIMENTS

It should be understood at the outset that although illustrative implementations of one or more embodiments are described below, the disclosed assemblies, systems and methods may be implemented using any number of techniques, whether currently known or not yet in existence. The disclosure should in no way be limited to the illustrative implementations, drawings, and techniques described below, but may be modified within the scope of the appended claims along with their full scope of equivalents.

The following brief definition of terms shall apply throughout the application:

The phrases "in one embodiment," "according to one embodiment," and the like generally mean that the particular feature, structure, or characteristic following the phrase may be included in at least one embodiment of the present invention and may be included in more than one embodiment of the present invention (importantly, such phrases do not necessarily refer to the same embodiment.

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the field of the art;

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiment, or it may be excluded.

Embodiments of the invention will now be described with reference to the figures, in which like numerals reflect like elements throughout. The terminology used in the description presented herein is not intended to be interpreted in any restrictive or limited way, simply because it is being utilized in conjunction with the detailed description of certain specific embodiments of the invention. Furthermore, embodiments of the invention may include several novel features, no single one of which is solely responsible for its desirable attributes, or which is essential to practicing the invention described herein.

Figure 1:
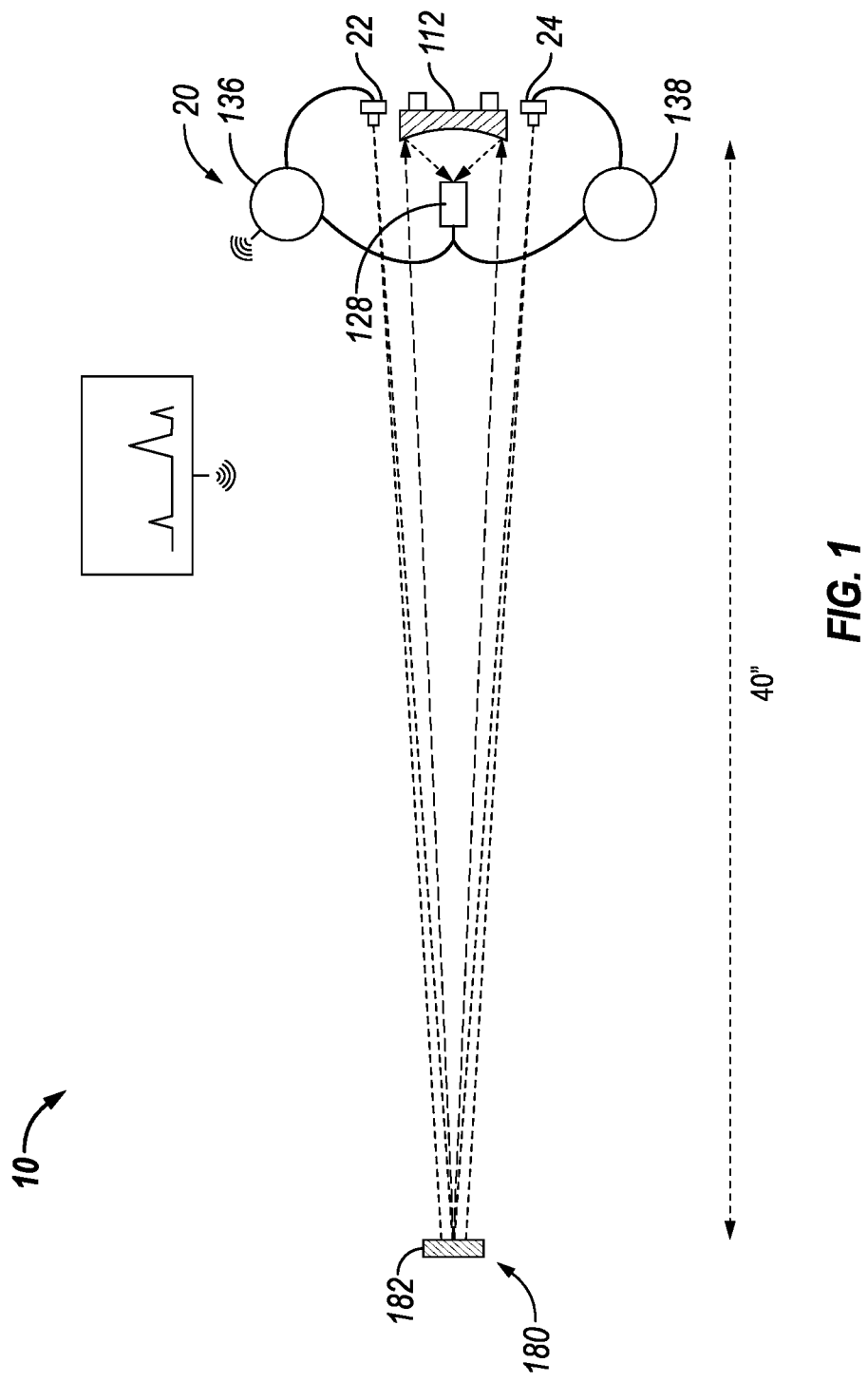
FIG. 1 is a schematic diagram of an embodiment of the system for simultaneous high-sensitivity measurement of methane and ethane via laser absorption spectroscopy.
Figure 9:
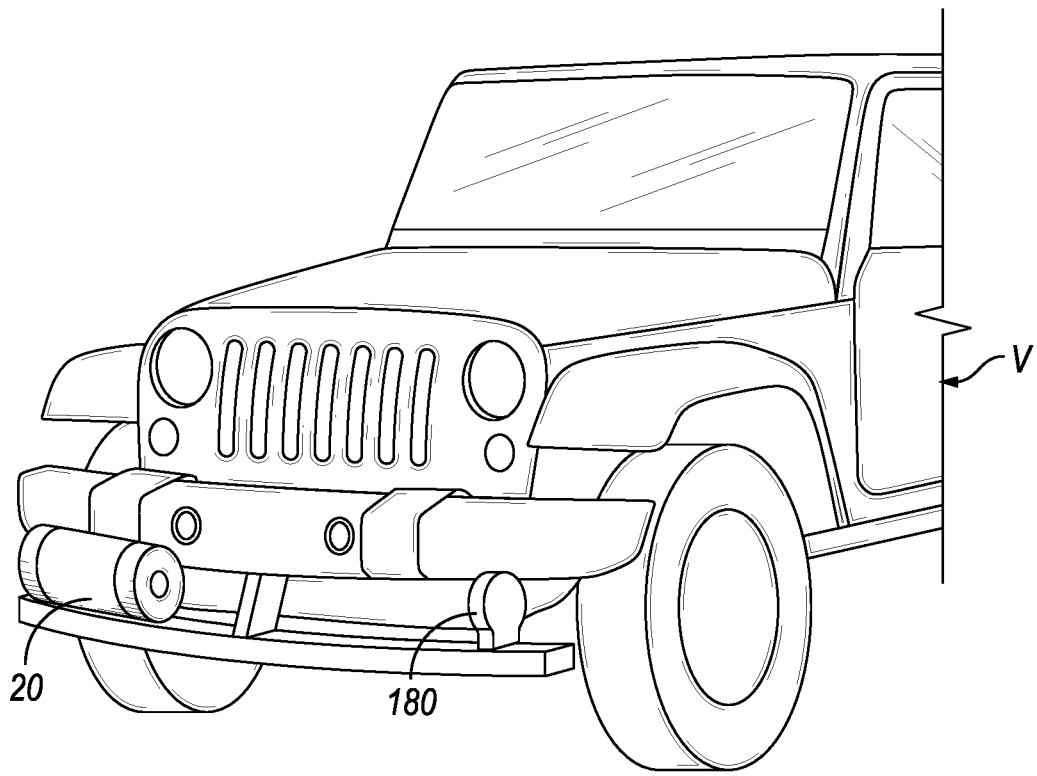
FIG. 9 is an perspective view of a natural gas leak survey vehicle having the system for simultaneous high-sensitivity measurement of methane and ethane mounted thereto, the system including the electro-optic package and a laser backscatter target package.

A schematic diagram of an embodiment of the system for simultaneous high-sensitivity measurement of methane and ethane via laser absorption spectroscopy, generally referenced as system 10, is shown in FIG. 1. The system 10 comprises an electro-optic package 20 and a laser backscatter target package 180 separated by approximately 1+/−0.3 meter suitable for attachment to a natural gas leak survey vehicle V as shown in FIG. 9.

With reference to a preferred embodiment shown in FIG. 1, the electro-optic package 20 includes first and second lasers, 22 and 24 respectively, preferably mid-infrared distributed feedback interband cascade lasers (mid-IR DFB-ICLs). Preferably, the first laser 22 is for the detection of ethane and the second laser 24 is for the detection of methane. Each laser's wavelength is selected to correspond with a specific target gas spectral absorption line that, when combined with the system optical design and signal processing method, provides desired sensitivity to the target gas and is free from cross-sensitivity to non-target gases. The optical configuration of FIG. 1 allows frequency multiplexing of two independent open-air laser spectrometers.

Still referring to FIG. 1, the electro-optic package 20 further comprises a primary concave mirror 112 and a detector 128. Laser light backscattered from the target 182 of the laser backscatter target package 180 is received by the concave mirror 112. The mirror 112 images the illuminated target spot onto the detector 128. The diameter and focal length of the mirror 112, as well as the optical characteristics of the scattering target disk 182, are designed to provide an electronic signal-to-noise ratio that does not limit measurement precision. The electrical output signal of the detector 128 is split into two sets of demultiplexing electronics included in electronic circuitry 136 and 138.

With reference to FIGS. 1, 4 and 4A, the two laser sources or packages 22, 24 are preferably mounted separately on a transmitter plate 66, which also serves as a heat sink. It is to be understood that the laser packages 22, 24 are commercially available products comprising a laser device within a can or housing attached to an enclosure 23. The can has a sealed window at an end opposite the enclosure 23. Although not shown, the laser package 22, 24 includes a thermistor attached to an internal submount, typically a copper platform. One side of the submount sits upon a thermoelectric cooler which is attached to the can. Heat is transferred from the thermoelectric cooler to the external heatsink via a laser mount subassembly 64.

The output light from each laser 22, 24 is collimated by a lens 100 (FIG. 4A), preferably also mounted to the transmitter plate 66. With reference to FIG. 1, the collimation creates laser beams that propagate to the distal scattering target 182 of the laser backscatter target package 180 and have beam diameters of a few millimeters when impinging on the target 182. In a preferred embodiment as shown in FIGS. 5, 5A and 5B, to optimize the quality of collimation, each laser source 22, 24 is mounted to a laser mount block 68 of a laser mount subassembly 64. Each laser mount subassembly 64 provides for fine adjustments of the laser source position relative to its corresponding lens 100 as will be discussed below. The two lasers 22, 24 are selected to emit approximately the same output power. In a preferred embodiment, the ethane laser is a Nanoplus 3336.8 nm DFB-ICL, and the methane laser is a Nanoplus 3291.1 nm DFB-ICL, products of Nanosystems and Technologies GmbH, Germany.

Figure 10:
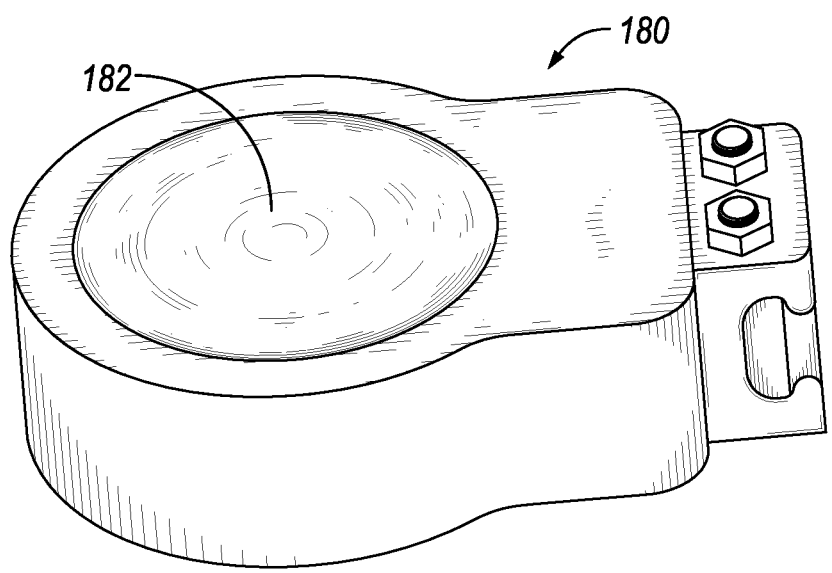
FIG. 10 is a perspective view of the laser backscatter target package shown in FIG. 9.

Referring to FIGS. 1, 9 and 10, the beams of the two lasers 22, 24 are projected onto the target or disk 182, preferably a directionally-reflective disk, of the distal laser backscatter target package 180. The term "directionally-reflective" means generally reflects light substantially back towards its source. Preferably, the directionally-reflective disk 182 is oriented substantially perpendicular (normal) to the laser propagation direction. The directionally-reflective disk 182 permits deviation from normal orientation of roughly +/−20 degrees during operation. The two laser beams impinge the target 182 within a detector optics field of view. Preferably, the two laser beams impinge at the same spot on the target 182, i.e. the beams overlap at the target 182.

In a preferred embodiment, the disk material of the directionally-reflective disk 182 is RC-301112-0000-NP, a product of Safe Reflections, Inc., Saint Paul, MN, or a similar material that provides reflectance at the laser wavelengths sufficient to achieve the desired laser power at the detector 128.

Referring to FIG. 10, the laser backscatter target package 180 may also comprise a target attachment platform and in preferred embodiments a battery-powered motor. The target disk 182 may be in continuous motion, for example by spinning around its axis, to reduce effects of laser speckle on system accuracy.

In a preferred embodiment, the detector 128 (FIGS. 1 and 6A) of the electro-optic package 20 is an uncooled photodetector, preferably a mercury-cadmium-telluride photodetector, with spectral bandwidth and optical configuration selected to optimize signal-to-noise response to received laser light. A preferred detector 128 is a photovoltaic optically immersed detector available from VIGO System SA.

The electro-optic package 20 includes electronic circuits 136, 138 to operate each laser 22, 24. Circuitry and associated firmware of the electronic circuits 136, 138 control laser temperature and laser current. Current to each laser 22, 24 is modulated at a distinct frequency. Preferably, the current to the methane laser is modulated at 8 kHz and 10 kHz to the ethane laser. The firmware provides adjustment for both parameters. The combination of laser temperature and current sets the laser wavelength to the designated methane and ethane spectral absorption feature. The circuitry also provides for a continual sinusoidal modulation of laser current, and thus laser wavelength. The modulation is typically set to repeatedly scan the laser wavelength across the spectral absorption feature, thus enabling the sensitive WMS detection technique. The methane modulation frequency differs from the ethane modulation frequency. This enables separating the signals received by the detector 128 and processing them individually in parallel via the technique known as Frequency Multiplexing. Applicant herein incorporates by reference U.S. Pat. Nos. 7,075,653 and 9,797,798 in their entireties.

Figure 11:
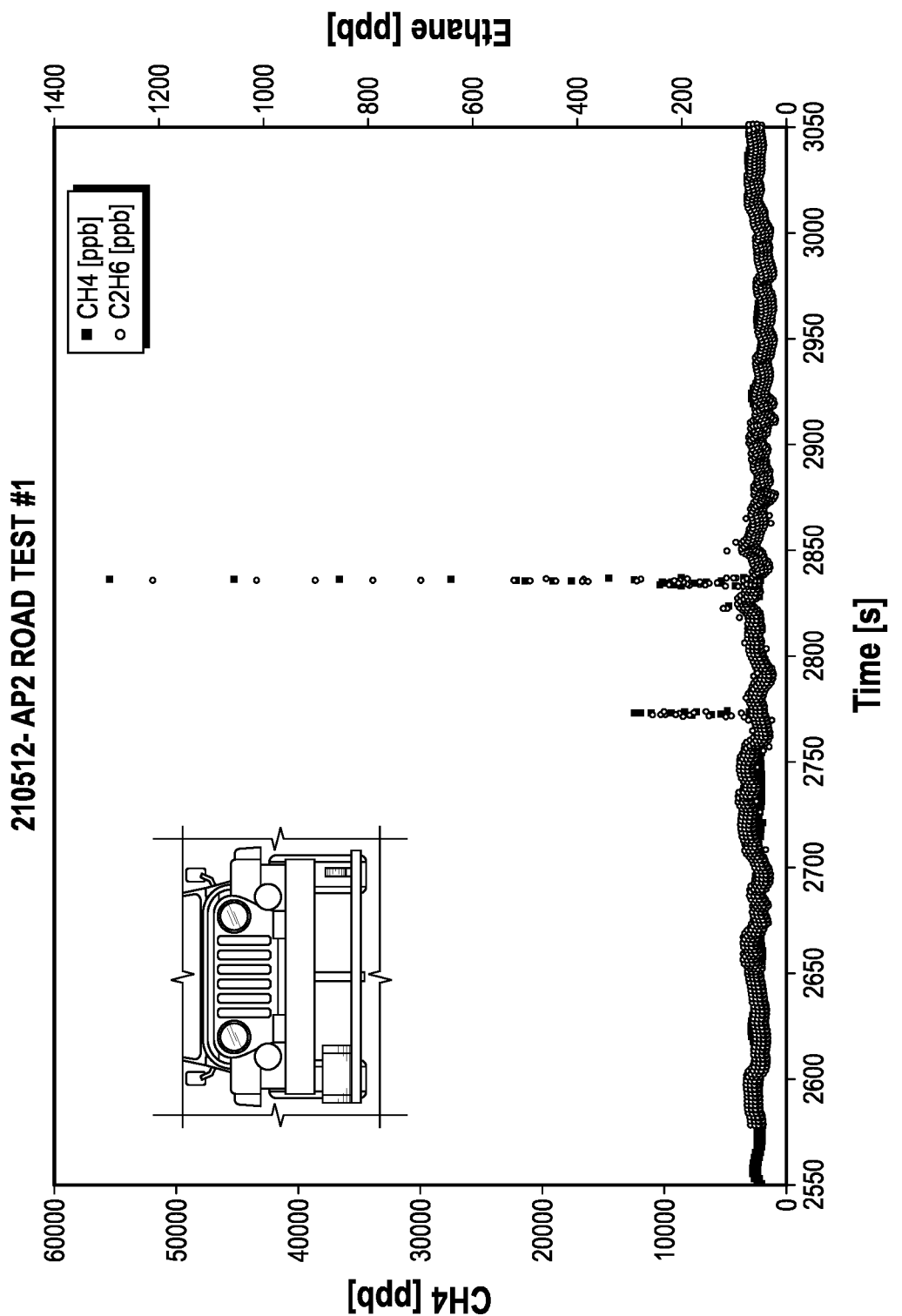
FIG. 11 is a graph showing the detection of ethane and methane in ppb versus time using an embodiment of the present invention.

The electronic circuits 136, 138 process the signals. The electronic circuits include firmware to demodulate the detector signals and produce outputs from which target gas concentrations are deduced within the firmware. The firmware also includes a capability to automatically tune each laser's wavelength to the peak of its spectral absorption line. FIG. 11 presents exemplary output target gas concentration as a function of time during a leak survey using a preferred embodiment of the invention. The graph displays methane and ethane concentrations measured by the invention with the invention deployed on a vehicle driving through an area of natural gas leakage. The spikes of highly elevated concentration occur when the vehicle passes directly through the plume of gas emanating from the leak source.

FIG. 2 is a perspective view of the electro-optic package 20 according to an embodiment of the invention. In a preferred embodiment, the electro-optic package 20 is compact, lightweight and battery-operated. Preferably, the battery-operated electro-optic package 20 weighs approximately four pounds (4 lbs) and comprises a cylindrical housing nominally less than 6 inches in diameter and 12 inches in length, and more preferably approximately 4.25 inches in diameter and approximately 9.5 inches long.

FIG. 2A is an exploded view of the electro-optic package 20 shown in FIG. 2. The electro-optic package 20 comprises a generally cylindrical housing 26 for housing an electro-optic internal assembly 28 which will be described in greater detail below. A front cap 30, preferably elastomeric, fits over and onto a front end of the electro-optic internal assembly 28 and the housing 26 as shown in FIGS. 2 and 2A.

A rear cap subassembly 32 mounts to a rear end of the housing 26 and a rear cap 34, preferably elastomeric, fits over and onto a rear end of the rear cap subassembly 32 and the housing 26 as shown in FIGS. 2 and 2A. A battery pack subassembly 36 is arranged and designed to be received through an opening in the rear cap 34 and connect with the rear cap subassembly 32.

Figure 2B:
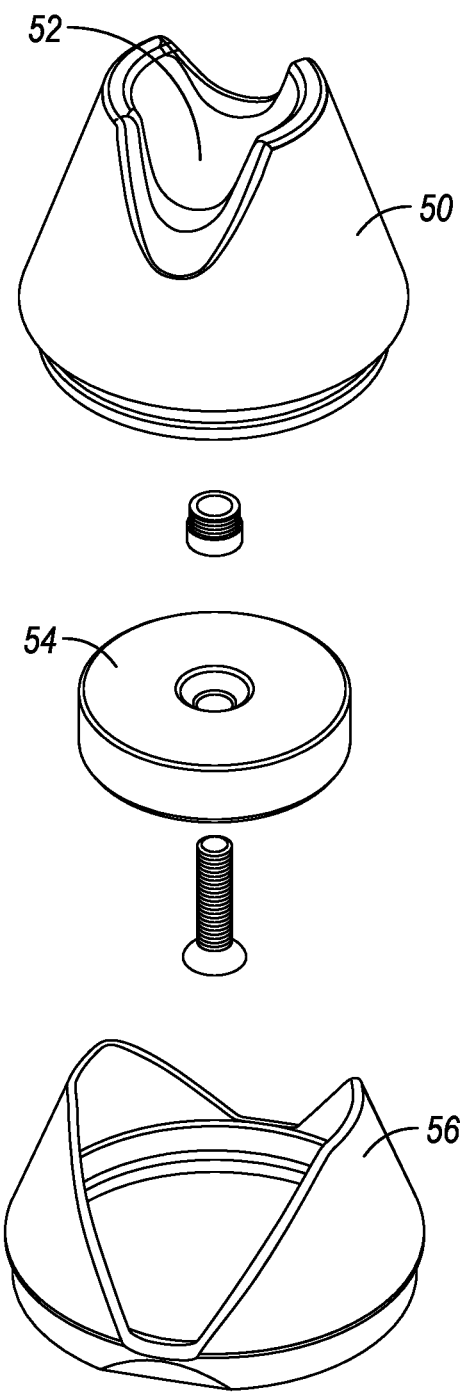
FIG. 2B is an exploded view of a foot assembly of a base assembly shown in FIG. 2A.

With reference to FIG. 2A, the electro-optic package 20 may include a base assembly 38 comprising a base member 40, preferably elongate, arranged and designed to be secured to the housing 26. In the illustrated embodiment, the base assembly 38 includes a pair of front legs 42 and a pair of rear legs 44 connected to the base member 40. In a preferred embodiment the distal end of each leg 42, 44 includes a foot assembly 46, preferably a pivotal foot assembly. Referring to FIGS. 2A and 2B, a ball knob 48, preferably made of polypropylene, is attached to the distal end of the leg 42, 44. The foot assembly 46 includes a foot 50 having a generally frustoconical shape and an opening 52 therethrough. The ball knob 48 is retained within the upper end of the foot opening 52. A magnet 54 is secured within the lower end of the foot opening 52 and a foot pad 56 is secured to a lower end of the foot 50. The magnets 54 in the four foot assemblies 46 may be used to secure the electro-optic package 20 to the front end of the natural gas leak survey vehicle V (FIG. 9) by being placed on a ferromagnetic metal. The base assembly 38 has not been shown in FIG. 9 for purposes of simplicity and clarity; however, it is to be understood that the system 10 comprising the electro-optic package 20 and the laser backscatter target package 180 is arranged and designed such that it may be mounted to the front of the natural gas leak survey vehicle V. It is to be further understood that the system 10 may be attached or mounted to the natural gas leak survey vehicle V by various means other than the base assembly 38.

FIGS. 3 and 3A are views of the electro-optic internal assembly 28 of the electro-optic package 20 shown in FIG. 2A. The electro-optic internal assembly 28 comprises a transmitter plate assembly 58, an optical receiver assembly 60 and a printed circuit board (PCB) stack subassembly 62. The transmitter plate assembly 58 is shown in greater detail in FIGS. 4 and 4A; the optical receiver assembly 60 in FIGS. 6, 6A and 6B; and the PCB stack subassembly 62 in FIGS. 7 and 7A.

With reference to FIGS. 4 and 4A, the transmitter plate assembly 58 includes a pair of laser mount subassemblies 64 mounted to a rear face of the transmitter plate 66. In a preferred embodiment, the position of each laser mount is adjustable to facilitate alignment with the corresponding lens 100. The laser mount subassembly 64 is shown in greater detail in FIGS. 5 and 5A. The laser mount subassembly 64 includes a laser mount block 68 having a front face 68f, rear face 68r, and a pair of side faces 68s. A generally rectangular recess 69 is formed in the front face 68f and defines a rear wall 69r, a pair of side walls 69s and an outer wall 69o as shown in FIG. 5A. The front face 68f includes a pair of side flanges 69f having a hole 69h therethrough.

Referring to FIG. 5A, a plurality of small holes 70 extend through the rear wall 69r of the laser mount block 68. The plurality of small holes 70 are spatially arranged to receive a plurality of prongs 72 of one of the laser packages 22, 24. The plurality of laser prongs 72 extend through the rear wall 69r and make contact with a printed circuit board 74. As shown in FIGS. 5 and 5A, the laser package 22, 24 preferably includes the laser enclosure 23 with holes 23h, and the rear wall 69r and a mounting bracket 75 connected to the printed circuit board 74 include similarly spaced holes. Fasteners 76, preferably screws, washers, and nuts, secure the laser package 22, 24 in the block recess 69 with the laser prongs 72 extending through the rear wall 69r and connecting with the printed circuit board 74. The holes for the prongs 72 in the mounting bracket 75 are not shown in FIG. 5A.

In a preferred embodiment, the laser mount subassembly 64 includes a plurality of plungers 78, preferably press-fit spring plungers, received in plunger openings 80 in the laser mount block 68 and a plurality of fine adjusters 82, preferably threaded adjusters. With reference to FIG. 5A, preferably each fine adjuster 82 is threadedly received within a bushing 84. Holes 86 are formed in the laser mount block 68 for receiving the bushings 84. Each bushing 84 has an annular outward-extending flange 84f to locate and position the bushing within the hole 86. In the embodiment shown in FIG. 5A, the fine adjusters 82 have a hex socket at one end adapted to receive an allen wrench for adjustment purposes.

Referring to FIGS. 4 and 4A, the transmitter plate 66 is preferably machined and includes a central optics window opening 66w. The central optics window opening 66w passes the received backscattered light to the primary mirror 112 (FIG. 3A). An optics window 88 is mounted to the transmitter plate 66 in the window opening 66w. In a preferred embodiment, the optics window material is anti-reflection coated sapphire. Preferably, an O-ring 90 is positioned between the optics window 88 and the transmitter plate 66 and a retaining ring 92 secures the optics window 88 to the transmitter plate 66.

As shown in FIG. 4A, the transmitter plate 66 preferably includes a pair of positioner blocks 94 for the laser mount subassemblies 64. The positioner block 94 and transmitter plate 66 include a laser hole 94h extending therethrough. The positioner block 94 has a pair of sides 94s with each side 94s having a medial cut-out portion 94c leaving first and second planer side faces 94f. The positioner block 94 includes a planer outer surface 94o located between the pair of side faces 94f.

Referring to FIGS. 4 and 4A, the transmitter plate 66 includes a pair of positioner tabs 96 spatially located relative to each positioner block 94. Each laser mount subassembly 64 is slid onto the positioner block 94 with the outer wall 69o (FIG. 5A) of the laser mount block 68 received between the planer outer surface 94o of the positioner block 94 and the pair of positioner tabs 96. Preferably, a first pair of spring plungers 78 (FIG. 5B) in the outer wall 69o abuts the pair of positioner tabs 96 and a second pair of spring plungers 78 (FIG. 5) in the side wall 69s abuts the first and second side faces 94f of one side 94s of the positioner block 94. The second side wall 69s of the laser mount block 68 includes a pair of fine adjusters 82 (FIG. 5B) for contacting the first and second side faces 94f of the second side 94s of the positioner block 94 and the fine adjuster 82 in the outer wall 69o is arranged to contact the outer surface 94o of the positioner block 94.

Referring to FIGS. 4 and 4A, a spring 98s and washer 98w are installed on a pair of mounting fasteners 98. The mounting fasteners 98 are inserted through the side flange holes 69h of the laser mount block 68 and threaded to an opening in the transmitter plate 66. The spring-loaded fasteners 98 maintain an axial spring force against the laser mount block 68 in the direction of the transmitter plate 66.

It is to be understood that the laser mount subassemblies 64 may be laterally finely adjusted via the combination of the fine adjusters 82 and the spring plungers 78. It is further to be understood that upon mounting the laser mount subassemblies 64 to the transmitter plate 66, the lasers 22, 24 are directed through the laser holes 94*h* in the positioner block 94 and the transmitter plate 66. An optical component 100, preferably an aspheric lens, and O-ring are aligned with the laser holes 94*h* and mounted to the transmitter plate 66 on the opposite side of the lasers 22, 24. With reference to FIG. 1, in order to provide flexibility in the distance between the electro-optics package 20 and the distal scattering target 182 wherein the two laser beams impinge the target 182 within the detector 128 field of view, the relative angle of the two lasers 22, 24 is minimized by minimizing the physical separation of the two laser sources within the mechanical constraints of the transmitter plate 66.

Still referring to FIGS. 4 and 4A, in one embodiment a green spotter laser source and PCB 102 is mounted to the transmitter plate 66 via a green spotter clamp 104 and insulation 106. The green spotter laser source and PCB 102 emanate a green laser beam which is directed through an opening in the transmitter plate 66. The green laser beam aids the positioning of the scattering target disk 182 during setup.

As shown in FIGS. 3, 3A, 4 and 4A, a plurality of precision rods 108 are mounted to the transmitter plate 66 at one end and to the optical receiver assembly 60 at a second end.

FIGS. 6, 6A and 6B are views of the optical receiver assembly 60 shown in FIG. 3A. The optical receiver assembly 60 comprises a spider bracket 110 having a plurality of openings 110*o* therethrough. A primary mirror 112 is mounted on one side of the spider bracket 110 via a plurality of precision rods 114 and threaded fasteners 116. Preferably, the primary mirror 112 is mounted such that it is centered on the central axis of the spider bracket 110.

As shown in FIG. 6A, the spider bracket 110 includes a large central hole 118 that is interrupted by a plurality of radial spokes 120 which support a central ring 122. In the illustrated embodiment, two spokes 120 are 180° apart and one spoke is at 90° from the other two spokes, leaving approximately 180° of the large central hole 118 unobstructed other than a portion being obstructed by the central ring 122. A detector bushing 124 is received in the central ring 122. A preamp clamp 126 comprising substantially a semi-circular member 126*m* slightly larger than the diameter of the large central hole 118 has a pair of inwardly extending arms 126*a* at each end of the semi-circular member 126*m*. Preferably, the preamp clamp 126 is secured to the spider bracket 110 with the pairs of inwardly extending arms 126*a* aligned with the two radially aligned spokes 120. Preferably, the distal end of the arms 126*a* includes arcuate segments 126*s* that contact the detector bushing 124 and secure it to the central ring 122.

The primary mirror 112 images the backscattered light onto the detector 128. In a preferred embodiment, the detector 128 is an uncooled mercury-cadmium-telluride photodetector with spectral bandwidth and optical configuration selected to optimize signal-to-noise response to received laser light. A preferred photodetector 128 is a photovoltaic optically immersed device available from VIGO System SA. The photodetector 128 includes a preamp assembly 130 comprising circuitry and a mounting frame 130*f* Preferably, the mounting frame 130*f* is adapted to be secured to the pair of inwardly extending arms 126*a* of the semi-circular member 126*m* with the photodetector 128 received within the detector bushing 124.

FIGS. 7 and 7A are views of the PCB stack subassembly 62 shown in FIG. 3. The PCB stack subassembly 62 comprises a plurality of boards 140 spaced apart with a plurality of hollow spacers 142. In a preferred embodiment, the plurality of boards 140 are arranged in two groups. Referring to FIG. 7A, each group has a drive board 140*d*, a power board 140*p*, and an auxillary board 140*a*. Additionally, each group includes a WMS board 140*w*. Preferably, in one group the board 140*w* is an 8 kHz WMS board and in the other group the board 140*w* is a 10 kHz WMS board. As discussed above, the methane modulation frequency differs from the ethane modulation frequency. Preferably, the ethane electronics is at 10 kHz and the methane electronics is at 8 kHz.

Uniformly arranged and sized holes 140*h* formed through the boards 140 permit a fastener 144 to pass through, then a spacer 142 is slid onto the fastener 144, and the process repeated. With reference to FIG. 7A, the fastener 144 passes through drive board hole 140*h*, through spacer 142, through WMS board hole 140*h*, through another spacer 142, through power board hole 140*h*, through another spacer 142, through auxiliary board hole 140*h*, through another spacer 142, and then is secured to an internal mid bracket 146.

As shown in FIG. 7A, one internal mid bracket 146 is positioned at opposite ends of the two groups of boards 140. The fasteners 144 provide a secure mounting of each group of boards 140 to an internal mid bracket 146. Preferably, a plurality of internal alignment rails 148 are securely fastened to each internal mid bracket 146 to join the internal mid brackets 146 and stabilize the PCB stack subassembly 62. Preferably, an outer portion of the internal alignment rails 148 includes an outer rubber layer 148*r*.

Mounted to the rear internal mid bracket 146 is a power interface board (PIB) 150. The PIB 150 distributes battery power to the various other boards 140.

Figure 8:
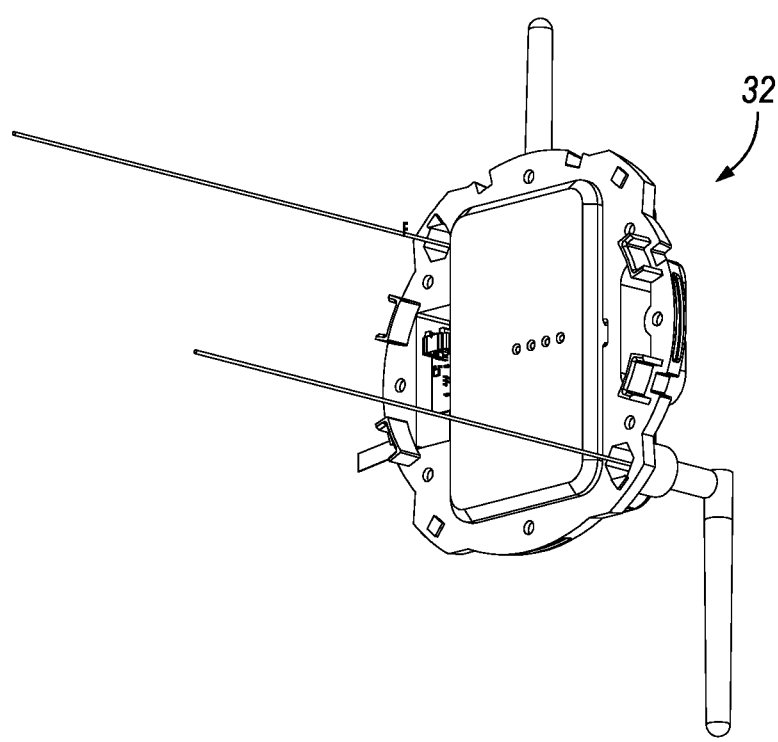
FIG. 8 is a perspective view of a rear cap subassembly shown in FIG. 2A.
Figure 8A:
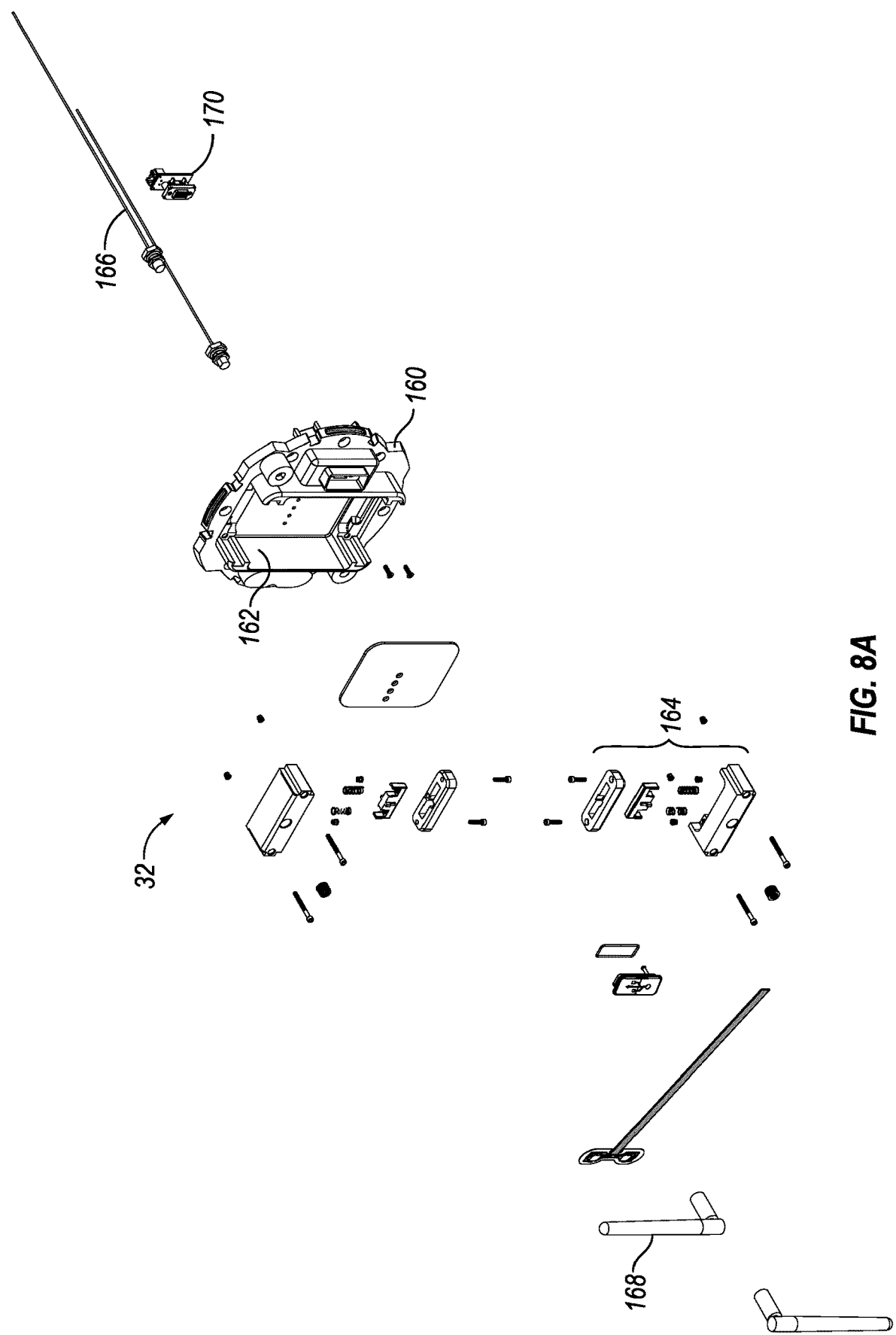
FIG. 8A is an exploded view of the rear cap subassembly shown in FIG. 8.

FIGS. 8 and 8A are views of the rear cap subassembly 32 shown in FIG. 2A. The rear cap subassembly 32 comprises a rear cap 160 having a battery retention slot 162, preferably with a detent mechanism 164 as shown in FIGS. 2A and 8A. Additionally, the rear cap subassembly 32 includes an antenna bulkhead 166 and an antenna 168, preferably a Bluetooth antenna. Preferably, a USB connector 170 is also provided for communication purposes.

It is to be understood that the electronics for the WMS and Frequency Multiplexing are available as off-the-shelf lab tools and a person of skill with this technology can reduce these tools to customized circuit boards. The system 10 includes electronic circuits 136, 138 as described above and summarized below.

First electronic circuitry to:

a) Fix the laser temperature by circuitry that receives and interprets the current produced by the thermistor within the laser package. A feedback circuit uses the difference between the measured temperature and the desired temperature to adjust the current supplied to a thermoelectric cooler within the laser package.

b) Control laser current with user-adjustable dc current source circuitry.

c) Modulate the laser current (and thus the laser wavelength and emitted laser power) by adding to the dc current a second current of user-adjustable amplitude that varies sinusoidally in time at a fixed frequency.

Second electronic circuitry are the same as first electronics but typically have values of temperature, dc current, modulation current, and modulation frequency that differ from values of the first electronics.

Third electronic circuitry receives the electrical signal produced by the detector. The signal is proportional to the backscattered laser light power impinging on the detector, including the modulation of laser power due to the current modulation at the fixed frequency, as well as modulation at harmonics of the fixed frequency due to spectral absorption by the target gas. The third electronic circuitry serves as lock-in amplifiers that demodulate the input signal and produce output signals that are proportional to the amplitude of the detector signal at the modulation frequency and at twice the modulation frequency. The ratio of these two outputs is proportional to the amount of target gas in the laser path.

When two lasers are frequency multiplexed, i.e. modulated at two different frequencies, then two sets of third electronic circuitry are used. One set demodulates only the first frequency and provides outputs from which the amount of the first target gas is deduced, while the second set demodulates only the second frequency.

NOMENCLATURE vehicle V
system 10
electro-optic package 20
first laser 22
enclosure 23
holes 23$h$
second laser 24
housing 26
electro-optic internal assembly 28
front cap 30
rear cap subassembly 32
rear cap 34
battery pack subassembly 36
base assembly 38
base member 40
front legs 42
rear legs 44
foot assembly 46
ball knob 48
foot 50
opening 52
magnet 54
foot pad 56
transmitter plate assembly 58
optical receiver assembly 60
PCB stack subassembly 62
laser mount subassemblies 64
transmitter plate 66
window opening 66$w$
laser mount block 68
front face 68$f$
rear face 68$r$
side faces 68$s$
recess 69
side flanges 69$f$
hole 69$h$
outer wall 69$o$
rear wall 69$r$
side walls 69$s$
small holes 70
laser prongs 72
printed circuit board 74
mounting bracket 75
fasteners 76
plungers 78
plunger openings 80
fine adjuster 82
bushing 84
flange 84$f$
holes 86 optics window 88
O-ring 90
retaining ring 92
positioner blocks 94
cut-out portion 94$c$
first and second planer side faces 94$f$
laser hole 94$h$
outer surface 94$o$
sides 94$s$
positioner tabs 96
fasteners 98
spring 98$s$
washer 98$w$
optical component 100
green spotter PCB 102
green spotter clamp 104
insulation 106
precision rods 108
spider bracket 110
openings 110$o$
primary mirror 112
precision rods 114
fasteners 116
central hole 118
spokes 120
central ring 122
detector bushing 124
preamp clamp 126
arms 126$a$
semi-circular member 126$m$
arcuate segments 126$s$
detector 128
preamp assembly
mounting frame 130$f$
ethane electronic circuits 136
methane electronic circuits 138
boards 140
auxillary board 140$a$
drive board 140$d$
holes 140$h$
power board 140$p$
wavelength modulation spectroscopy (WMS) board 140$w$
spacers 142
fastener 144
internal mid bracket 146
internal alignment rails 148
outer rubber layer 148$r$
PIB board 150
rear cap 160
battery retention slot 162
detent mechanism 164
antenna bulkhead 166
antenna 168
USB connector 170
laser backscatter target package 180
directionally-reflective disk 182
disk material
target attachment platform
battery-powered motor The foregoing disclosure and description of the invention are illustrative and explanatory thereof, and various changes in the size, shape and materials, as well as in the details of the illustrated construction, may be made without departing from the spirit of the invention. The present embodiment is, therefore, to be considered as merely illustrative and not restrictive, the scope of the invention being indicated by the claims rather than the foregoing description, and all changes

We claim:

1. A system for measuring a target gas via laser absorption spectroscopy in an open-air configuration, comprising:
   a mid-infrared distributed feedback interband cascade laser (mid-IR DFB-ICL) (22) having a wavelength selected to correspond with a spectral absorption line of the target gas;
   first electronic circuitry to control the laser temperature, current and modulation frequency;
   a heat sink (58) for the mid-IR DFB-ICL (22);
   a distal backscattering directionally-reflective target (182);
   an optical component (100) that projects a beam of the mid-IR DFB-ICL onto the distal backscattering directionally-reflective target (182);
   an optical receiver assembly (60) that receives a fraction of the laser light that is backscattered from the directionally-reflective target (182) and focuses the collected light onto an uncooled photodetector (128).

2. The system of claim 1, wherein the uncooled photodetector (128) is a photovoltaic optically immersed device.

3. The system of claim 1, wherein the uncooled photodetector (128) is a mercury-cadmium-telluride photodetector.

4. The system of claim 3, wherein the photodetector (128) has a spectral bandwidth and optical configuration selected to optimize signal-to-noise response to received laser light.

5. The system of claim 1, wherein the optical receiver assembly (60) comprises a primary mirror (112) for receiving laser light backscattered from the directionally-reflective target (182) and focusing the collected light onto the uncooled photodetector (128).

6. The system of claim 1, wherein the directionally-reflective target (182) comprises a material that provides reflectance at the laser wavelength sufficient to achieve a desired laser power at the photodetector (128).

7. The system of claim 6, wherein the target material is RC-301112-0000-NP, a product of Safe Reflections, Inc.

8. The system of claim 1, further comprising:
   the first electronic circuitry providing for a continual sinusoidal modulation of laser current and wavelength, the continual sinusoidal modulation set to repeatedly scan the laser wavelength across the spectral absorption feature at a selected modulation frequency to enable wavelength modulation spectroscopy; and
   electronic demodulation circuitry to demodulate the photodetector signal and produce outputs from which target gas concentrations are deduced.

9. The system of claim 1, wherein the open-air path length of the laser beam is approximately one meter.

10. The system of claim 9, wherein the laser wavelength is selected to provide a desired sensitivity to the target gas and is substantially free from cross-sensitivity to non-target gases.

11. The system of claim 10, wherein the target gas is methane and the laser wavelength is 3291.1 nm.

12. The system of claim 10, wherein the target gas is ethane and the laser wavelength is 3336.8 nm.

13. A system for simultaneously measuring methane and ethane in an open-air configuration, comprising:
   a first mid-infrared distributed feedback interband cascade laser (mid-IR DFB-ICL) (22) having a wavelength selected to correspond with a spectral absorption line of ethane;
   a second mid-infrared distributed feedback interband cascade laser (mid-IR DFB-ICL) (24) having a wavelength selected to correspond with a spectral absorption line of methane;
   first electronic circuitry to control the first laser temperature, current and modulation frequency;
   second electronic circuitry to control the second laser temperature, current and modulation frequency;
   a heat sink (58) for the first and second mid-IR DFB-ICLs (22, 24);
   a distal backscattering directionally-reflective target (182);
   a first optical component that projects a beam of the first mid-IR DFB-ICL (22) onto the distal backscattering directionally-reflective target (182);
   a second optical component that projects a beam of the second mid-IR DFB-ICL (24) onto the distal backscattering directionally-reflective target (182);
   an optical receiver assembly (60) that receives a fraction of the laser light that is backscattered from the directionally-reflective target (182) and focuses the collected light onto an uncooled photodetector (128).

14. The system of claim 13, wherein the modulation frequency of the first mid-IR laser differs from that of the second mid-IR laser.

15. The system of claim 14, wherein the beam projected from the first mid-IR laser and the beam projected from the second mid-IR laser substantially overlap each other at the distal backscattering directionally-reflective target.

16. The system of claim 13, wherein a transmitter plate assembly (58) supports the two lasers (22, 24) and serves as the laser heat sink.

17. The system of claim 16, wherein the first and second mid-IR DFB-ICLs (22, 24), the first and second electronic circuitry, the first and second optical components, the optical receiver assembly and the heat sink are arranged in a compact package adapted for mounting to a natural gas utility leak survey vehicle.

18. The system of claim 13, wherein the first laser wavelength is 3336.8 nm.

19. The system of claim 13, wherein the second laser wavelength is 3291.1 nm.

20. The system of claim 18, wherein the second laser wavelength is 3291.1 nm.

21. The system of claim 17, wherein the compact package is a cylindrical shape having a diameter less than 6 inches and a length less than 12 inches.

* * * * *